(12) United States Patent
Felder et al.

(10) Patent No.: US 9,095,340 B2
(45) Date of Patent: Aug. 4, 2015

(54) TISSUE STAPLER SAFETY SWITCH FEATURE TO PREVENT PREMATURE JAW OPENING

(75) Inventors: Kevin D. Felder, Cincinnati, OH (US); John F. Cummings, Madeira, OH (US); Joseph P. Schowalter, South Lebanon, OH (US); Patrick J. Swindon, Cincinnati, OH (US); Johnny H. Alexander, III, West Chester, OH (US); Christopher C. Miller, Loveland, OH (US); Barry T. Jamison, Fairfeld, OH (US); John V. Hunt, Cincinnati, OH (US); Kent P. Baker, Liberty Township, OH (US); Julia F. Serber, Brookline, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 737 days.

(21) Appl. No.: 13/344,071

(22) Filed: Jan. 5, 2012

(65) Prior Publication Data
US 2013/0175319 A1  Jul. 11, 2013

(51) Int. Cl.
*A61B 17/068* (2006.01)
*A61B 17/115* (2006.01)
*A61B 17/29* (2006.01)
*A61B 19/00* (2006.01)

(52) U.S. Cl.
CPC ..... *A61B 17/1155* (2013.01); *A61B 2017/2946* (2013.01); *A61B 2019/4857* (2013.01)

(58) Field of Classification Search
CPC ...................... A61B 17/068; A61B 2017/2946
USPC ................... 227/175.1, 175.2, 176.1; 606/219
See application file for complete search history.

(56) References Cited

U.S. PATENT DOCUMENTS

| 4,805,823 A | 2/1989 | Rothfuss |
| 5,137,198 A | 8/1992 | Nobis et al. |
| 5,205,459 A | 4/1993 | Brinkerhoff et al. |

(Continued)

FOREIGN PATENT DOCUMENTS

| EP | 1 815 805 | 8/2007 |
| WO | WO 2004/032760 | 4/2004 |

(Continued)

OTHER PUBLICATIONS

International Search Report dated Sep. 27, 2013 for Application No. PCT/US2012/069995.

(Continued)

*Primary Examiner* — Michelle Lopez
(74) *Attorney, Agent, or Firm* — Frost Brown Todd LLC

(57) ABSTRACT

A surgical stapler comprises an anvil assembly, an anvil shaft, a driver, an actuating arm, a safety switch, and a safety feature. The anvil assembly couples with the anvil shaft. The driver drives a plurality of staples into tissue. The actuating arm is in communication with the surgical stapler and is configured to actuate the driver to drive the plurality of staples into tissue. The safety switch is moveable between a locked and an unlocked position. The safety switch prevents operation of the actuating arm when the safety switch is in the locked position. The safety switch enables operation of the actuating arm when the safety switch is in the unlocked position. The safety feature may prevent operation of the driver even when the safety switch is in the unlocked position or prevent operation of the safety switch.

13 Claims, 13 Drawing Sheets

(56) References Cited

U.S. PATENT DOCUMENTS

| | | |
|---|---|---|
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,333,773 A | 8/1994 | Main et al. |
| 5,350,104 A | 9/1994 | Main et al. |
| 5,415,334 A | 5/1995 | Williamson, IV et al. |
| 5,465,895 A | 11/1995 | Knodel et al. |
| 5,533,661 A | 7/1996 | Main et al. |
| 5,597,107 A | 1/1997 | Knodel et al. |
| 5,632,432 A | 5/1997 | Schulze et al. |
| 5,673,840 A | 10/1997 | Schulze et al. |
| 5,685,474 A | 11/1997 | Seeber |
| 5,704,534 A | 1/1998 | Huitema et al. |
| 5,814,055 A | 9/1998 | Knodel et al. |
| 6,010,054 A | 1/2000 | Johnson et al. |
| 6,945,444 B2 | 9/2005 | Gresham et al. |
| 6,978,921 B2 | 12/2005 | Shelton, IV et al. |
| 7,000,818 B2 | 2/2006 | Shelton, IV et al. |
| 7,143,923 B2 | 12/2006 | Shelton, IV et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,721,930 B2 | 5/2010 | McKenna et al. |
| 2007/0010838 A1 | 1/2007 | Shelton, IV et al. |

FOREIGN PATENT DOCUMENTS

| | | |
|---|---|---|
| WO | WO 2010/045533 | 4/2010 |
| WO | WO 2013/090221 | 6/2013 |

OTHER PUBLICATIONS

International Preliminary Report on Patentability dated Jul. 8, 2014 for Application No. PCT/US2012/069995.

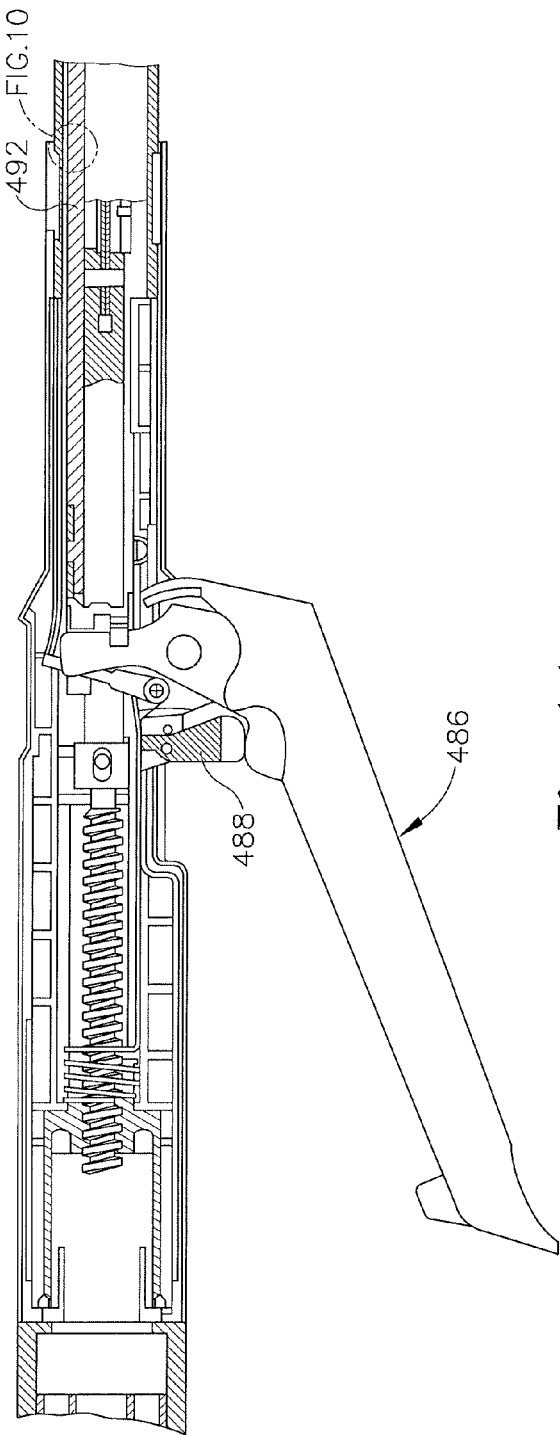
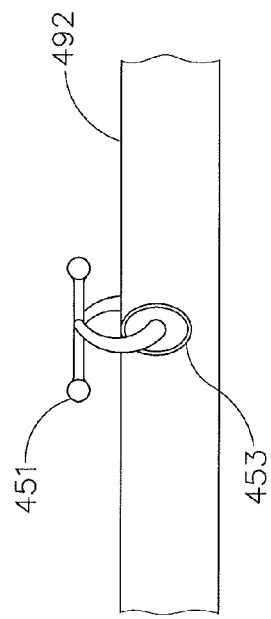

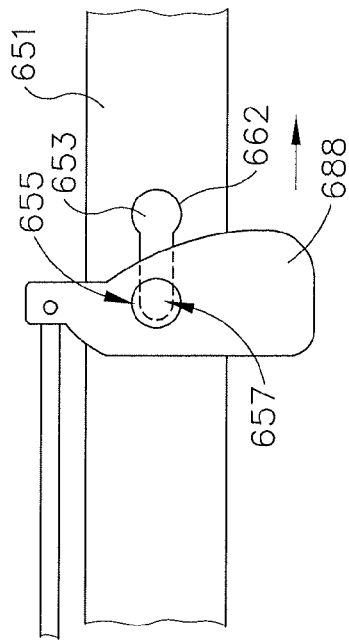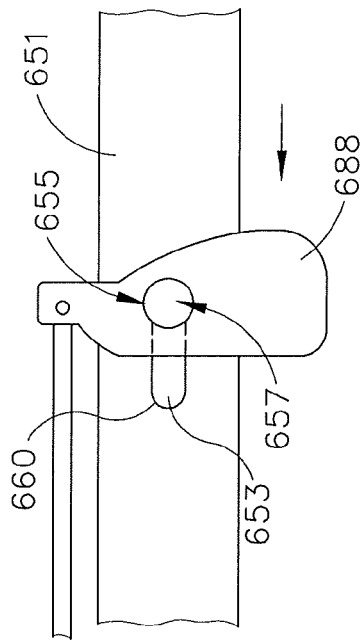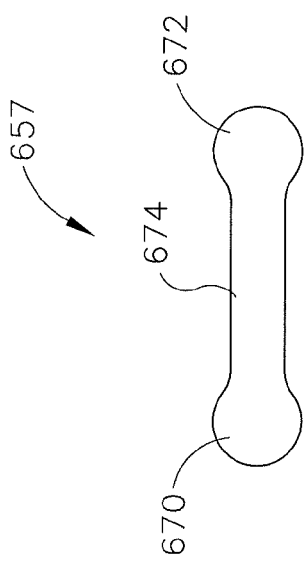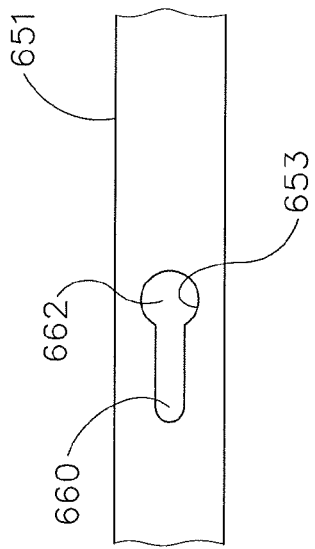

TISSUE STAPLER SAFETY SWITCH FEATURE TO PREVENT PREMATURE JAW OPENING

BACKGROUND

Generally, in the performance of a surgical anastomotic stapling operation, two pieces of lumen or tubular tissue, e.g., intestinal tissue, are attached together by a ring of staples. The two pieces of tubular tissue may be attached end to end or one piece of tubular tissue may be attached laterally around an opening formed in the side of another piece of tubular tissue. In performing the anastomosis with a stapling instrument, the two pieces of tubular tissue are clamped together between an anvil provided with a circular array of staple forming grooves and a staple holder provided with a plurality of staple receiving slots arranged in a circular array in which the staples are received. A staple pusher is advanced to drive the staples into the tissue and form the staples against the anvil. Also, a circular knife is advanced to cut the excess tissue clamped between the anvil and the staple holder. As a result, a donut-shaped section of tissue is severed from each lumen and remains on the anvil shaft. The tubular tissue joined by the circular ring of staples is unclamped by advancing the anvil shaft distally to move the anvil away from the staple holder. The stapling instrument is removed by pulling the anvil through the circular opening between the pieces of tubular tissue attached by the ring of staples.

Examples of such circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While a variety of surgical staplers have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 8 depicts a front view of an indictor window on top of the actuator handle assembly of FIG. 5;

FIG. 10 depicts a side view of a brake and driver actuating member inside the stapler instrument of FIG. 9;

FIG. 11 depicts a side, cross sectional view of the stapler instrument of FIG. 9;

FIG. 16 depicts a front, elevational view of a pin for use with the safety feature of FIG. 15;

FIG. 17A depicts a side view of the safety feature of FIG. 15 with an anvil rod in a distal position;

FIG. 17B depicts a side view of the safety feature of FIG. 15 with the anvil rod in a proximal position;

FIG. 18 depicts a side view of an exemplary anvil rod for use with the stapler instrument of FIG. 15;

Figure 1:
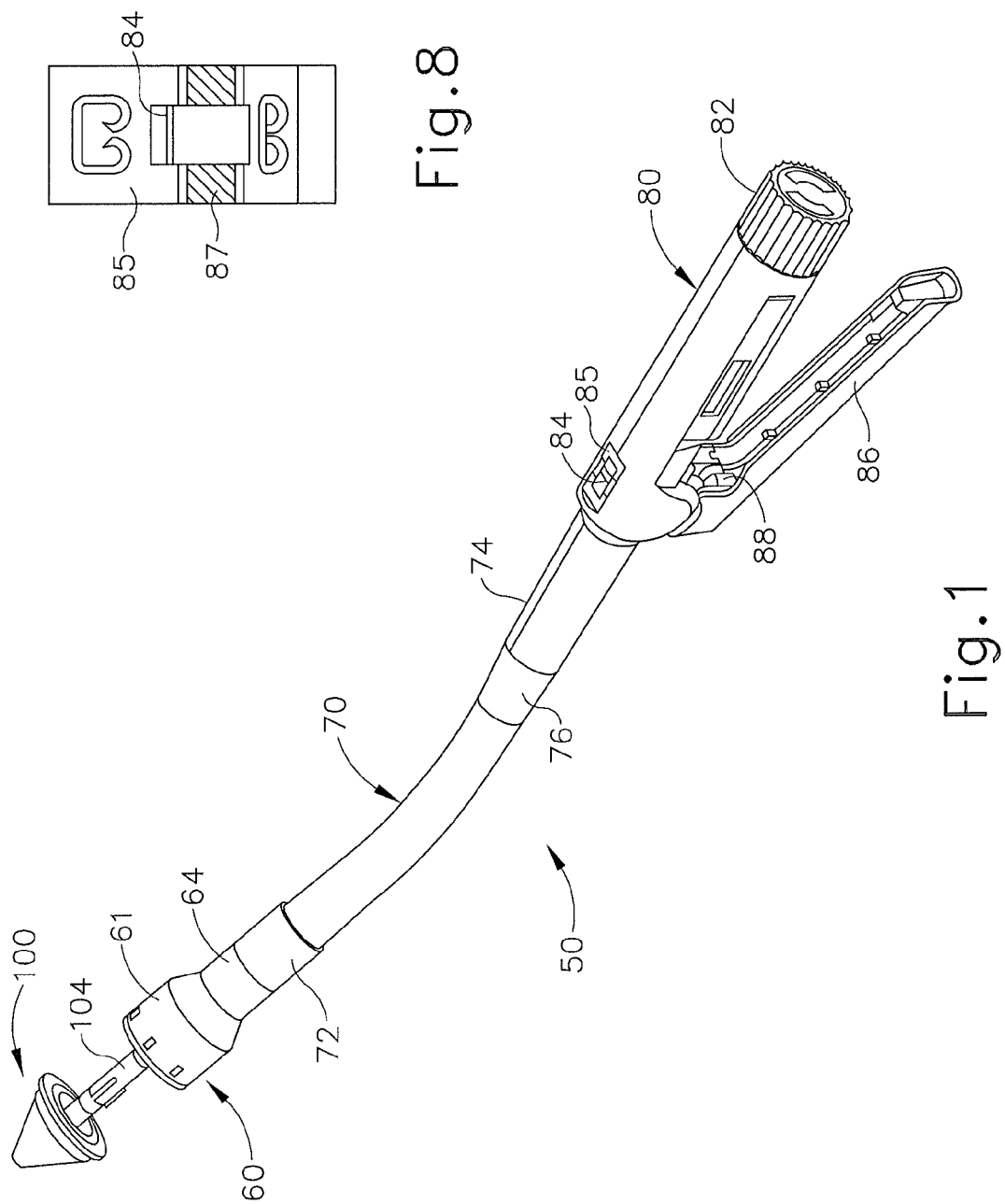
FIG. 1 depicts a perspective view of an exemplary stapler instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Stapling Instrument

FIG. 1 illustrates a circular anastomosis surgical stapling instrument (50) that includes a distal stapling head assembly (60) connected by a longitudinally curved support shaft assembly (70) to a proximal actuator handle assembly (80). Stapling instrument (50) may be constructed in accordance with at least some of the teachings of U.S. Pat. No. 5,205,459, entitled "Surgical anastomosis stapling instrument," issued on Apr. 27, 1993; U.S. Pat. No. 5,271,544, entitled "Surgical anastomosis stapling instrument," issued on Dec. 21, 1993; U.S. Pat. No. 5,275,322, entitled "Surgical anastomosis stapling instrument," issued on Jan. 4, 1994; U.S. Pat. No. 5,285,945, entitled "Surgical anastomosis stapling instrument," issued on Feb. 15, 1994; U.S. Pat. No. 5,292,053, entitled "Surgical anastomosis stapling instrument," issued on Mar. 10, 1993; U.S. Pat. No. 5,333,773, entitled "Sealing means for endoscopic surgical anastomosis stapling instrument," issued on Apr. 2, 1994; U.S. Pat. No. 5,350,104, entitled "Sealing means for endoscopic surgical anastomosis stapling instrument," issued on Sep. 27, 1994; and/or U.S. Pat. No. 5,533,661 entitled "Sealing means for endoscopic surgical anastomosis stapling instrument," issued on Jul. 9, 1996, the disclosures of which are incorporated by reference herein.

Stapling instrument (50) includes an anvil assembly (100) that is slidable longitudinally relative to stapling head assembly (60). A rotatable adjusting knob (82) is provided at the proximal end of actuator handle assembly (80) operable to adjust the spacing between stapling head assembly (60) and anvil assembly (100). Adjusting knob (82) is in communication with control rod (300) (shown, for example, in FIG. 5) such that rotation of adjusting knob (82) causes control rod (300) to translate. When adjusting knob (82) is rotated in one direction, the gap between stapling head assembly (60) and anvil assembly (100) closes, whereas when adjusting knob (82) is rotated in a different direction, the gap between stapling head assembly (60) and anvil assembly (100) opens. While the exemplary version comprises adjusting knob (82), it will be appreciated that a button, actuator, or any other suitable mechanism may be used in place of adjusting knob (82) as would be apparent to one of ordinary skill in the art in view of the teachings herein. In some versions, adjusting knob (82) may be operable to open the gap between stapling head assembly (60) and anvil assembly (100) in more than one manner. For example, adjusting knob (82) may be moveable in two positions once an operation is complete. In the first position, adjusting knob (82) may create a small gap, whereas in a second position, adjusting knob (82) may create a larger gap. Adjusting knob (82) may be moved to the first position, for example, when stapling instrument (50) is removed from a surgical site; and adjusting knob (82) may be moved to the second position, for example, to remove anvil assembly (100) from stapling head assembly (60). In some versions, the above described gap adjustment mechanism may be controllable through adjusting knob (82). In some other versions, a separate actuator may be integrated into stapling instrument (50) such that when the actuator is used to control the gap between stapling head assembly (60) and anvil assembly (100) after operation, adjusting knob (82) becomes locked out such that the user cannot subsequently operate adjusting knob (82).

Figure 5:
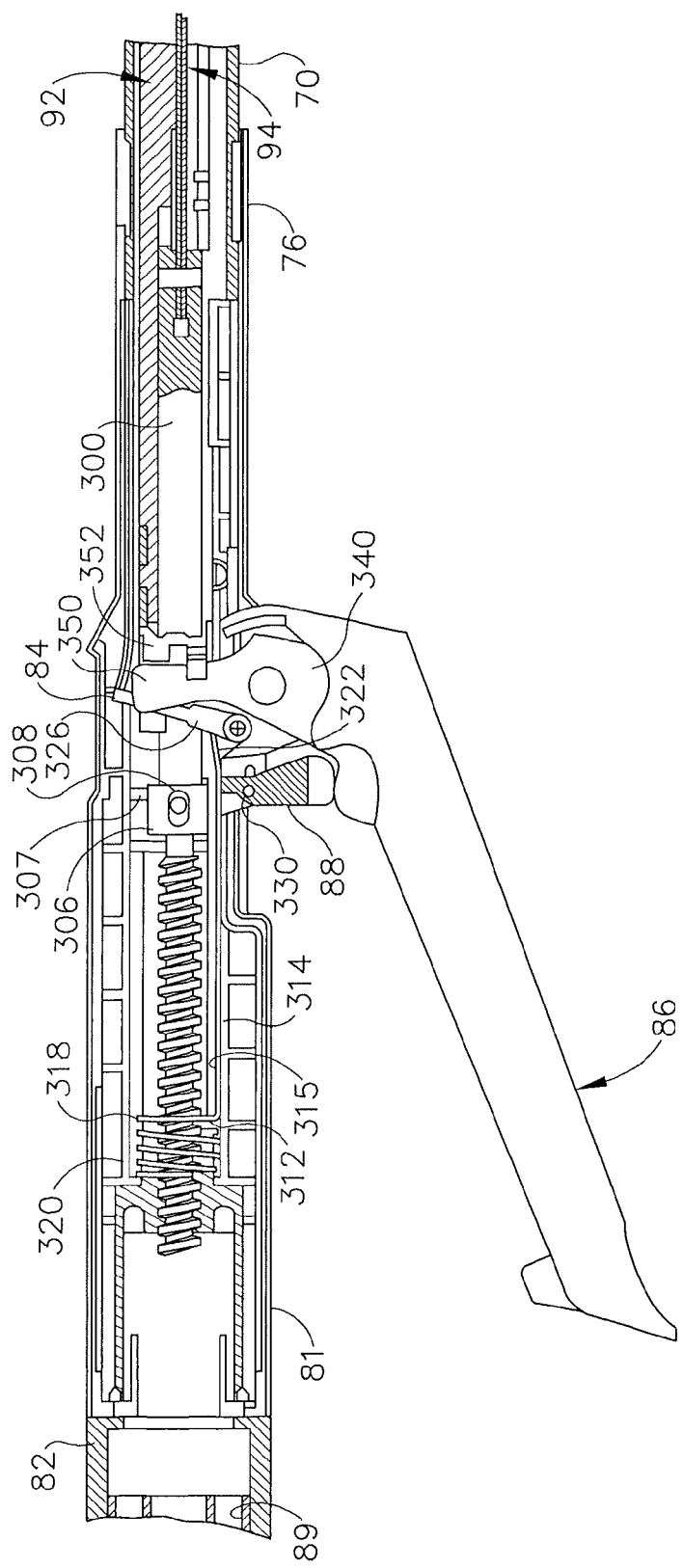
FIG. 5 depicts a side, cross sectional view of the stapler instrument of FIG. 1 showing the actuator handle assembly in a locked position.

A movable indicator (84) is visible through a window (85) on top of handle assembly (80) to indicate the staple height selected by rotation of adjusting knob (82). As shown in FIG. 5, indicator (84) is movable along a scale (87) which indicates that the anvil gap is within a desired operating range of stapling instrument (50). The position of indicator (84) also indicates whether the formed staple height will be large or small.

A staple actuating lever (86) is pivotally mounted on actuator handle assembly (80) for driving the surgical staples from stapling head assembly (60) when anvil assembly (100) is closed to provide the desired staple height. A pivotal safety latch (88) is mounted on handle assembly (80) for locking staple actuating lever (86) against movement to preclude actuation of stapling head assembly (60) when the anvil gap is outside of a predetermined range.

Figure 2:
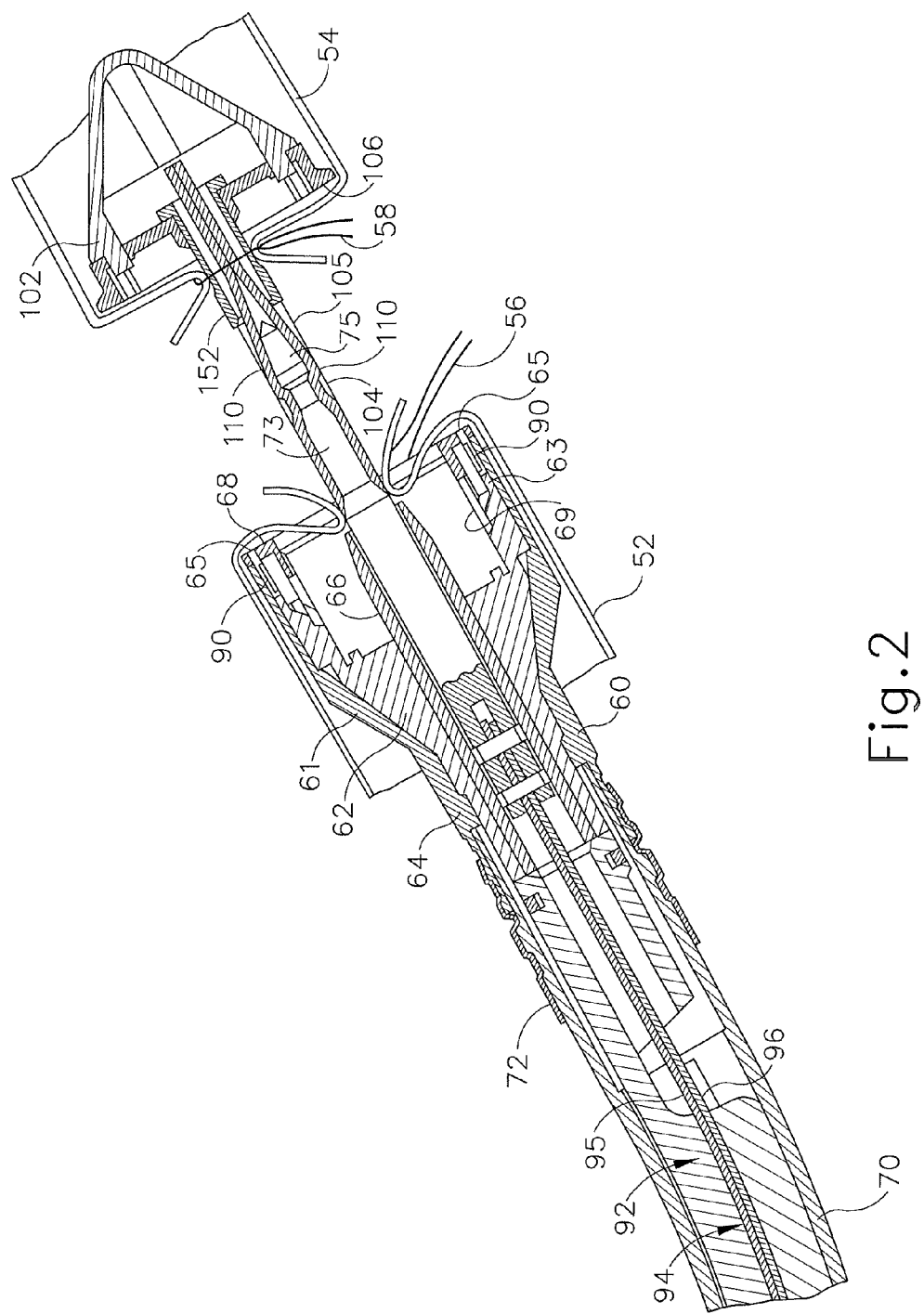
FIG. 2 depicts a side, cross sectional view of a stapling head assembly of the stapler instrument of FIG. 1.

Referring to FIG. 2, stapling head assembly (60) includes a tubular casing (61) which slidably receives a staple driver (62) which can be advanced and retracted by operation of actuator handle assembly (80). Staple driver (62) includes a plurality of fingers (63) for engaging and driving a plurality of staples (90) from a staple holder (68) mounted at the distal end of casing (61). Staple holder (68) includes a plurality of staple receiving slots (65) into which staples (90) are inserted. Staple driver (62) further supports a circular knife and/or scalpel (69) which is advanced and retracted with staple driver (62).

Stapling head assembly (60) includes a hollow tubular connector (64) at the proximal end of casing (61) which receives the distal end of support shaft (70). A ferrule or sleeve (72) overlaps the joint between tubular connector (64) and the distal end of support shaft (70). Similarly, the proximal end of support shaft (70) is received by a tubular extension (74) at the distal end of actuator handle assembly (80). A ferrule or sleeve (76) overlaps the joint between the proximal end of support shaft (70) and the distal end of tubular extension (74).

Still referring to FIG. 2, anvil assembly (100) includes a generally circular anvil (102) mounted on a hollow axially extending shaft (104) which is detachably secured to a trocar (73) slidably supported by stapling head assembly (60). Trocar (73) includes a pointed trocar tip (75) which is inserted into a hollow sleeve (105) at the proximal end of anvil shaft (104). While the illustrated version shows one exemplary orientation for trocar (73) and anvil shaft (104), it will be appreciated that in some versions, the position of trocar (73) and anvil shaft (104) may be reversed such that trocar (73) is positioned on anvil assembly (100) and pointed towards stapling head assembly (60). Other suitable variations may be used as would be apparent to one of ordinary skill in the art in view of the teachings herein. Trocar (73) is slidably received within a central support tube (66) (shown in FIG. 2) formed on tubular casing (61) for longitudinal movement relative to staple holder (68) mounted at the distal end of casing (61). Staple receiving slots (65) in staple holder (68) are arranged in a circular array for receiving surgical staples (90). Staple receiving slots (65) of the exemplary version are arranged in two closely spaced concentric annular rows. Anvil (102) includes an annular rim (106) having a plurality of staple forming grooves for forming staples (90) when driven against anvil (102).

Anvil assembly (100) includes a pair of elongated, spring-like retainer clips (110) extending longitudinally along anvil shaft (104) for engaging trocar tip (75) when trocar (73) is inserted into anvil shaft (104). To facilitate the insertion of trocar (73) into anvil shaft (104), trocar tip (75) has a low force profile. In the exemplary version, trocar tip (75) is tapered at a shallow angle to reduce the force required to bias open retainer clips (110).

Figure 3:
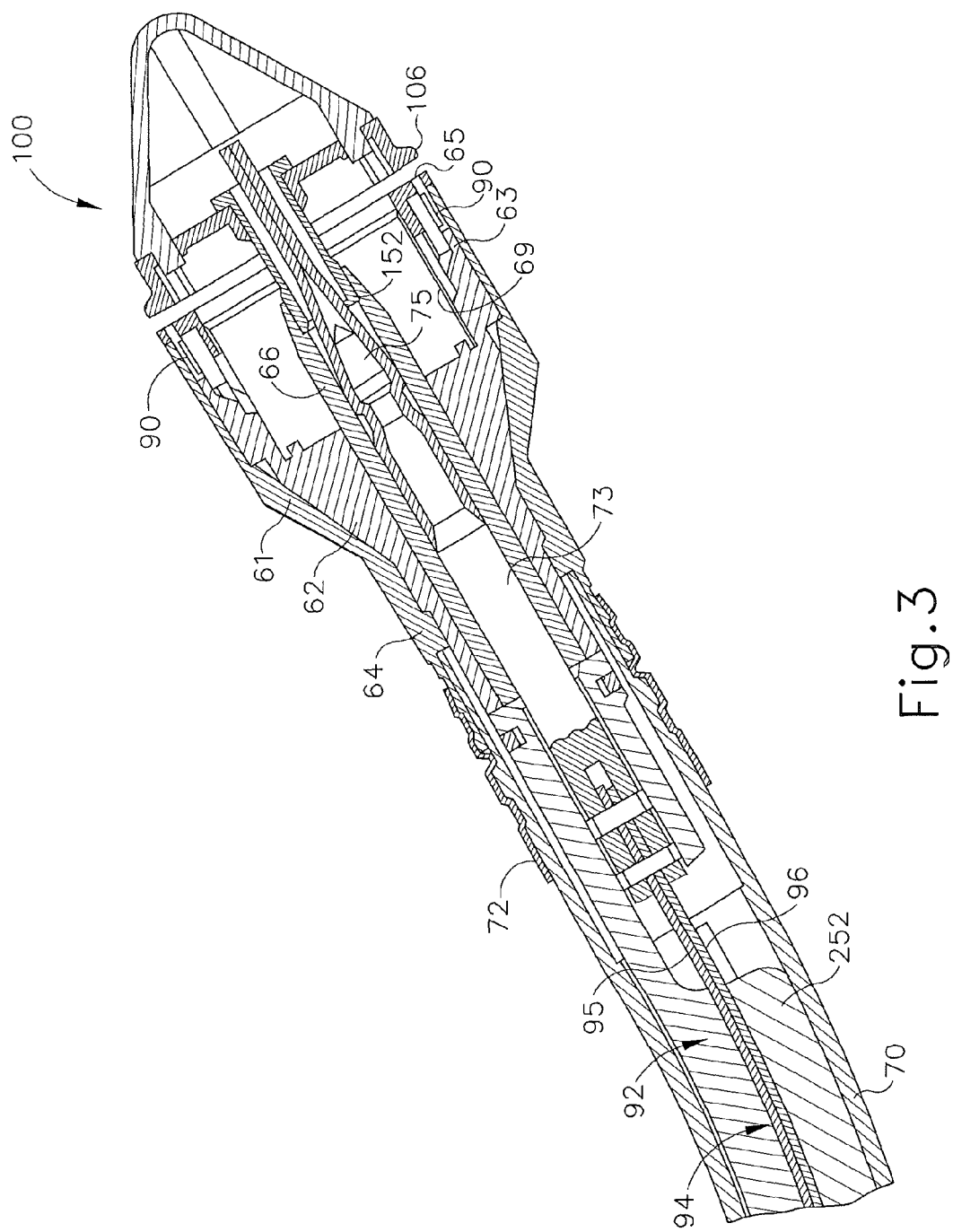
FIG. 3 depicts a side, cross sectional view of the stapling head assembly of FIG. 2 in a closed position.

Retainer clips (110) permit anvil assembly (100) to be attached to or detached from trocar (73) by pushing or pulling, respectively, on anvil assembly (100). With stapling instrument (50) in its closed position as shown in FIG. 3, trocar (73) is retracted into central support tube (66) which restricts radial movement of retainer clips (110) so that detents are held in place against trocar tip (75). As a result, anvil assembly (100) is locked to trocar (73) so that anvil (102) can resist the full firing force of stapling instrument (50) without disengagement of retainer clips (110) from trocar tip (75).

Raised circumferential section (152) defines a circumferential notch on anvil shaft (104) which is convenient for purse stringing of the tubular tissue. As shown in FIG. 2, if the tissue is tightly purse stringed to shaft (104), the purse stringed tissue cannot easily slip over raised circumferential section (152). As a result, the purse stringed tissue is confined to the distal region of anvil shaft (104) beyond raised circumferential section (152) and anvil shaft (104) cannot inadvertently slip through the purse stringed tissue.

Figure 4:
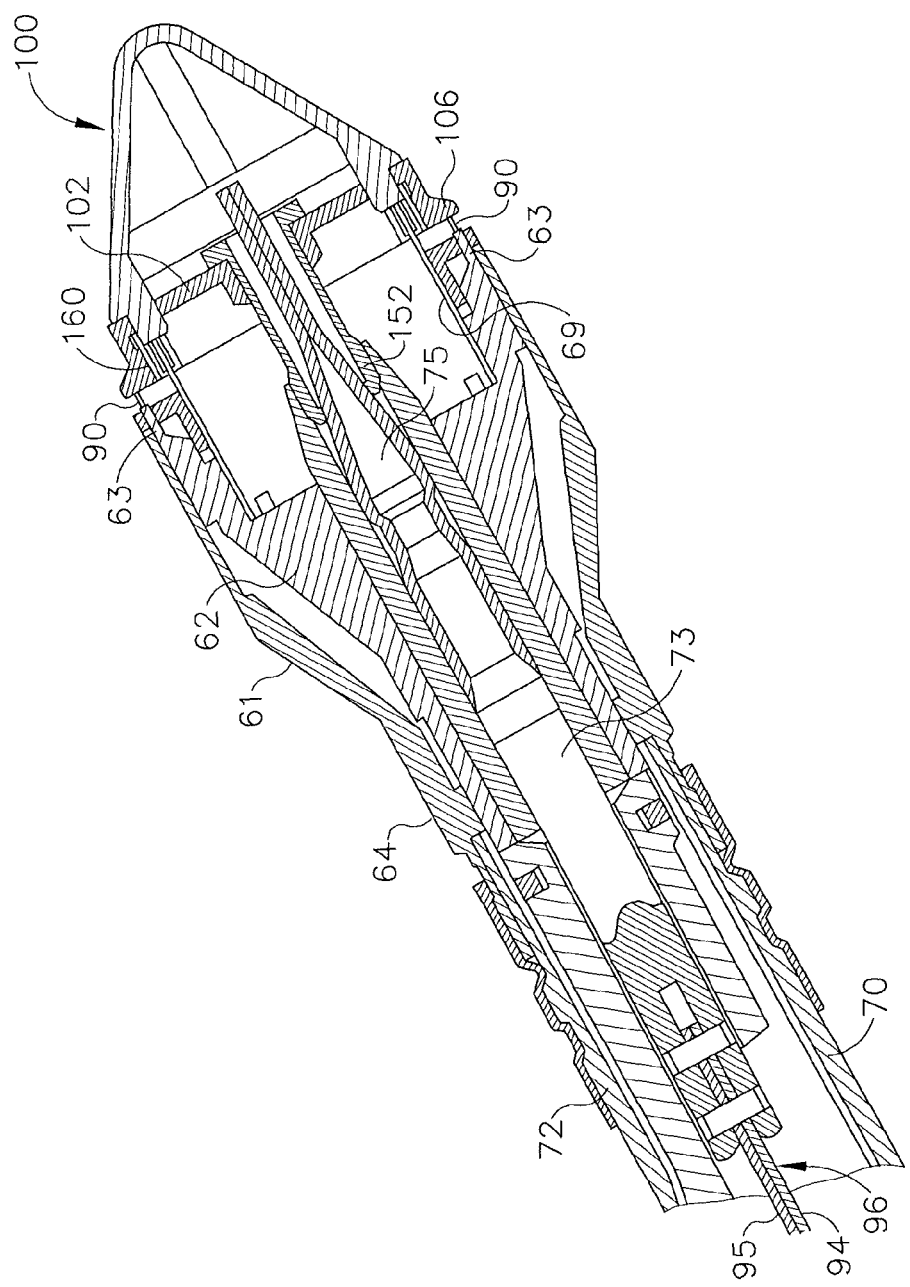
FIG. 4 depicts a side, cross sectional view of the stapling head assembly of FIG. 2 showing a staple driver in a fired position.

Referring to FIGS. 4 and 5, support shaft (70) contains a driver actuating member (92) operable to transmit compressive forces and motion from actuator handle assembly (80) to operate staple driver (62) in stapling head assembly (60). Also, support shaft (70) contains a tension member (94) comprising a pair of elongated flexible bands (95, 96) operable to transmit the tension from actuator handle assembly (80) to anvil assembly (100) to resist the compressive forces exerted on anvil assembly (100). Tension bands (95, 96) transmit longitudinal motion from actuator handle assembly (80) to allow anvil assembly (100) to be adjusted in position relative to stapling head assembly (60). In particular, tension member (94) is coupled with control rod (300) such that tension member (94) and control rod (300) translate unitarily. An elongated flexible spacer band is contained within the space between support shaft (70) and flexible tension bands (95, 96). By rotating adjusting knob (82) in the counterclockwise direction, as viewed, for example, in FIG. 1, control rod (300) is advanced to move tension member (94) in the distal direction to open the gap between anvil assembly (100) and stapling head assembly (60). A stop (307) (shown in FIG. 5) on one of handle sections (81) engages screw (308) to limit the distal movement of control rod (300). By rotating adjusting knob (82) in the opposite direction, i.e., clockwise, control rod (300) is retracted to move tension member (94) in the proximal direction to close the gap between anvil assembly (100) and stapling head assembly (60). A stop (309) on cap (89) limits the proximal movement of control rod (300).

Stapling instrument (50) further comprises a safety release bracket (312), which is translated based on movement of control rod (300). In particular, a clip (306) that is secured to control rod (300) is configured to engage an upstanding flange (318) of safety release bracket (312) when control rod (300) reaches a certain proximal position. Thereafter, continued proximal movement of control rod (300) will move safety release bracket (312) proximally. A coil spring (320) is positioned between flange (318) and a rib (315) of handle assembly (80), and thereby provides a distal bias to safety release bracket (312). Thus, when safety release bracket (312) is in a proximal position and control rod (300) is advanced distally, coil spring (320) will move safety release bracket (312) distally. Safety release bracket (312) is operable to control the movement of indicator (84). In particular, safety release bracket (312) is operable to communicate movement to an indicator lever (326) via a transversely oriented finger of safety release bracket (312), based on the longitudinal position of control rod (300). Indicator (84) is integrally formed at a free end of indicator lever (326).

Figure 6:
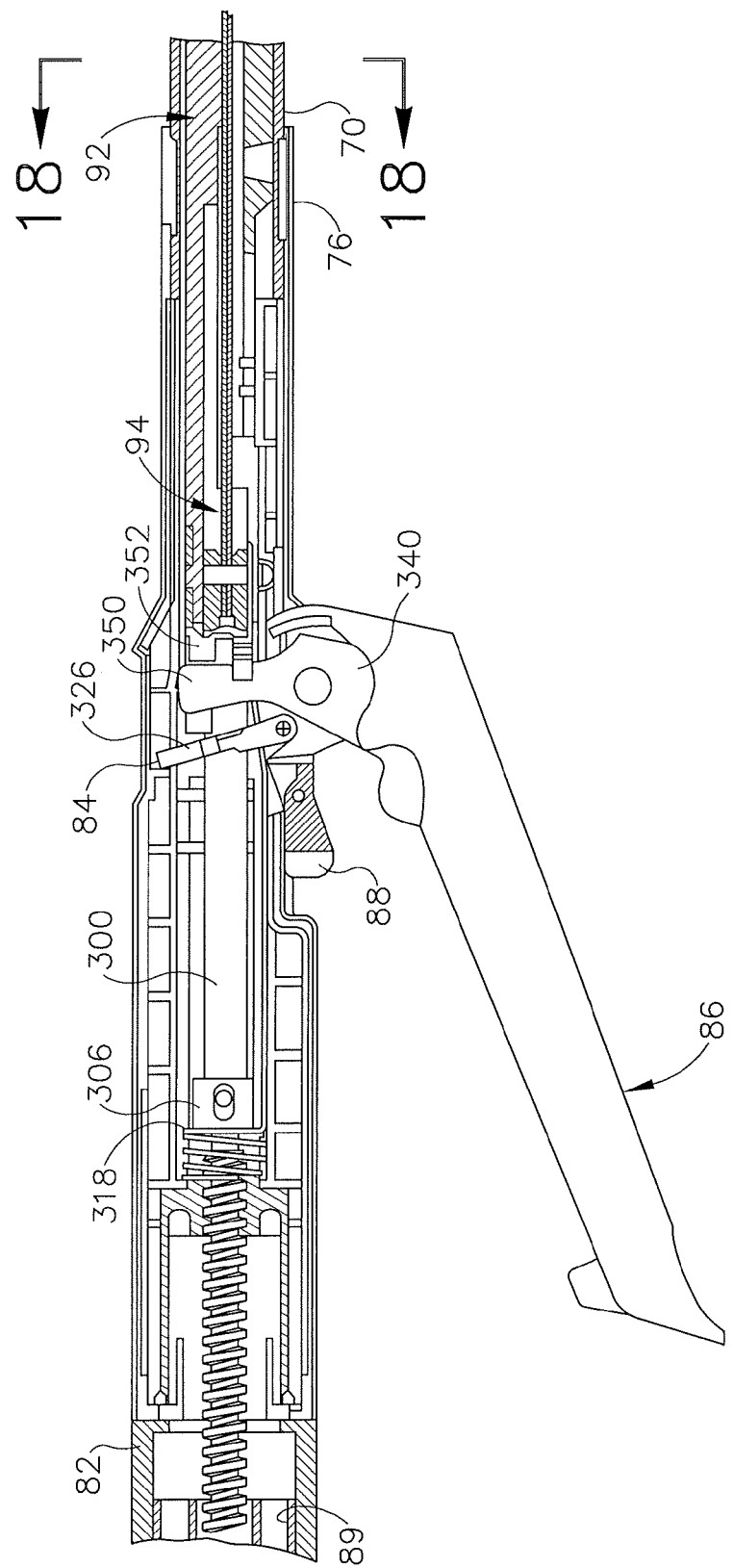
FIG. 6 depicts a side, cross sectional view of the actuator handle assembly of FIG. 5 in an unlocked position.

In FIGS. 2 and 5, stapling instrument (50) is shown with anvil assembly (100) fully open and actuator handle assembly (80) in an unfired and unlocked configuration. With anvil assembly (100) fully open, safety release bracket (312) is biased distally by coil spring (320) to urge upstanding flange (318) against rib (315) with the transverse finger of safety release bracket (312) advanced distally and disengaged from indicator lever (326). When control rod (300) is retracted, as shown in FIG. 6, clip (306) on control rod (300) is moved in a proximal direction to engage flange (318) and move safety release bracket (312) in the proximal direction. Initially, as anvil assembly (100) begins to close, the transverse finger of safety release bracket (312) remains disengaged from indicator lever (326). When the gap between anvil assembly (100) and stapling assembly (60) is adjusted into a predetermined range of the instrument, the finger engages and pivots indicator lever (326) to move indicator (84) proximally along scale (87) on window (85) to provide an indication of the selected staple height to be produced when the stapling instrument is fired.

Safety release bracket (312) is also operable to selectively prevent movement of safety latch (88). In particular, as will be described in greater detail below, a portion of safety release bracket (312) physically obstructs pivotal movement of safety latch (88) when control rod (300) is outside of a predetermined longitudinal range; while safety release bracket (312) enables pivotal movement of safety latch (88) when control rod (300) is within the predetermined longitudinal range. Such a longitudinal range may correlate with a preferred range of formed staple heights at anvil assembly (100).

Safety latch (88) is pivotally mounted beneath safety release bracket (312) by a pivot pin (330) extending between handle sections (81). Safety latch (88) is operable to physically prevent actuating lever (86) from being squeezed. For example, in one position shown in FIG. 5, safety latch (88) blocks actuation of actuating lever (86). In another position shown in FIG. 6, safety latch (88) is moved to permit actuation of actuating lever (86). Safety latch (88) includes a ledge that, in its latched position, is disposed horizontally underneath safety release bracket (312). If the anvil gap is outside the predetermined range of the stapling instrument (shown in FIGS. 2 and 5), rectangular plate (314) of safety release bracket (312) overlaps ledge on safety latch (88) and prevents safety latch (88) from being disengaged from staple actuating lever (86). On scale (87), the user can see movable indicator (84) falling outside the zone indicated by scale (87). On the other hand, when the anvil gap is within the predetermined range (shown in FIGS. 3 and 6), safety release bracket (312) is retracted and ledge on safety latch (88) is disengaged from rectangular plate (314) of safety release bracket (312). Safety latch (88) can be pivoted to its unlatched position to enable staple actuating lever (86) to be operated. It will be appreciated that as movable indicator (84) moves into the zone shown by scale (87), movable indicator (84) may be utilized as a visual signal to the user that stapling instrument (50) may be fired.

When the gap between anvil (102) and staple holder (68) is set to produce a desired staple height within the operating range of stapling instrument (50), safety latch (88) is pivoted clockwise to disengage staple actuating lever (86). Stapling instrument (50) is fired by grasping and pivoting staple actuating lever (86) clockwise to move staple actuating lever (86) to its operative position. As a result, actuator fingers (350) on trigger arm (340) drive firing clip (352) in the distal direction to advance driver actuating member (92) longitudinally along shaft assembly (70). Driver actuating member (92) advances staple driver (62) to move driver fingers (63) distally in staple receiving slots (65) to engage staples (90). Driver actuating member (92) transmits the required motion and compressive forces from trigger arm (340) to staple driver (62) to drive staples (90) from staple holder (68) into tissue and against anvil (102). Each staple (90) is formed into a B-shaped configuration to staple tissue sections (52, 54) together. Also, circular knife (69) is advanced by staple driver (62) to cut the tissue against backup washer (160). As shown in FIG. 4, circular knife (69) splits backup washer (160) into two annular sections.

After the stapling and cutting of the tissue is completed, staple actuating lever (86) is biased by a spring back to its open, unactuated position shown in FIG. 5. Actuator fingers (350) of trigger arm (340) pivot counterclockwise, as viewed in FIG. 6, to move firing clip (352) and driver actuating member (92) in the proximal direction. As a result, staple driver (62), which is connected by locator fingers to driver actuating member (92), and circular knife (69) are retracted into stapling head assembly (60).

Stapled tissue between anvil (102) and staple holder (68) is released by rotating adjusting knob (82) counterclockwise to advance anvil assembly (100) away from stapling head assembly (60) e.g., by approximately ½ of a turn or ¾ of a turn, etc. Anvil (102) is moved through the lumen by manipulating the stapled tissue in a suitable manner to slip the anvil through the stapled lumen. Then, stapling instrument (50) is withdrawn from the patient leaving behind the stapled lumen between tubular tissue sections (52, 54).

Surgical stapling instrument (50) can be used to perform an intraluminal anastomosis in which two sections of tissue are attached together by an array of staples. By way of example, stapling instrument (50) may be used in a procedure for joining a pair of hollow organ sections (e.g., in a patient's colon or other section of gastro-intestinal tract) end to end with a plurality of surgical staples arranged in a circular array around a hollow lumen between the organ sections. In preparation for the anastomosis, purse string sutures are placed in the hollow organs to be anastomosed. For example, as shown in FIG. 2, two tubular tissue sections (52) and (54) are prepared by threading purse string sutures (56) and (58), respectively, into the tissue in purse string fashion adjacent to the open ends of tubular tissue sections (52) and (54).

If the surgical procedure is performed using a double purse string suturing technique, stapling instrument (50) is inserted into first tubular tissue section (52), e.g., by insertion into the anal opening of the patient, with anvil assembly (100) attached to stapling head assembly (60) and completely closed. Prior to insertion of stapling instrument (50) into the patient, adjusting knob (82) is rotated clockwise to retract trocar (73) into support tube (66) and to clamp anvil (102) against staple holder (68). Stapling head assembly (60) is positioned adjacent to purse stringed end of tubular tissue section (52). Next, adjusting knob (82) is rotated clockwise to advance control rod (300) and tension member (94) until trocar (73) is fully advanced to move anvil assembly (100) to its fully open position (FIG. 2). With trocar (73) fully advanced, the purse stringed end of tubular tissue section (52) is drawn together about cylindrical trocar body (130) by pulling and tightening purse string suture (56). The purse stringed tissue is drawn against cylindrical trocar body (130) and purse string suture (56) is tied to hold the tissue against trocar body (130).

Anvil assembly (100) is inserted into the purse stringed end of the tubular tissue section (54) and the tissue is drawn together about anvil shaft (104) by pulling and tightening purse string suture (58). The purse stringed tissue is pulled against anvil shaft (104) in tying notch (158) distally adjacent to raised circumferential section (152) on anvil shaft (104) and purse stringed suture (58) is tied together. If desired, anvil assembly (100) may be detached from trocar (73) to facilitate the insertion of anvil assembly (100) into tubular tissue section (54). After the purse stringed end of tubular tissue section (54) is tied against anvil shaft (104) by purse string suture (58), anvil assembly (100) is re-attached to trocar (73).

After the purse stringed ends of tubular tissue sections (52) and (54) are tied, adjusting knob (82) is rotated clockwise to retract trocar (73) into support tube (66) to move anvil (102) toward staple holder (68). As trocar (73) is retracted, trocar body (130) slides through the purse stringed end of tissue section (52) in the proximal direction to pull anvil shaft (104) through the purse stringed tissue into support tube (66). Stapling instrument (50) eventually reaches the configuration shown in FIG. 3. Actuator handle assembly (80) remains in the fully advanced or open configuration shown in FIG. 5 during this transition.

Figure 7:
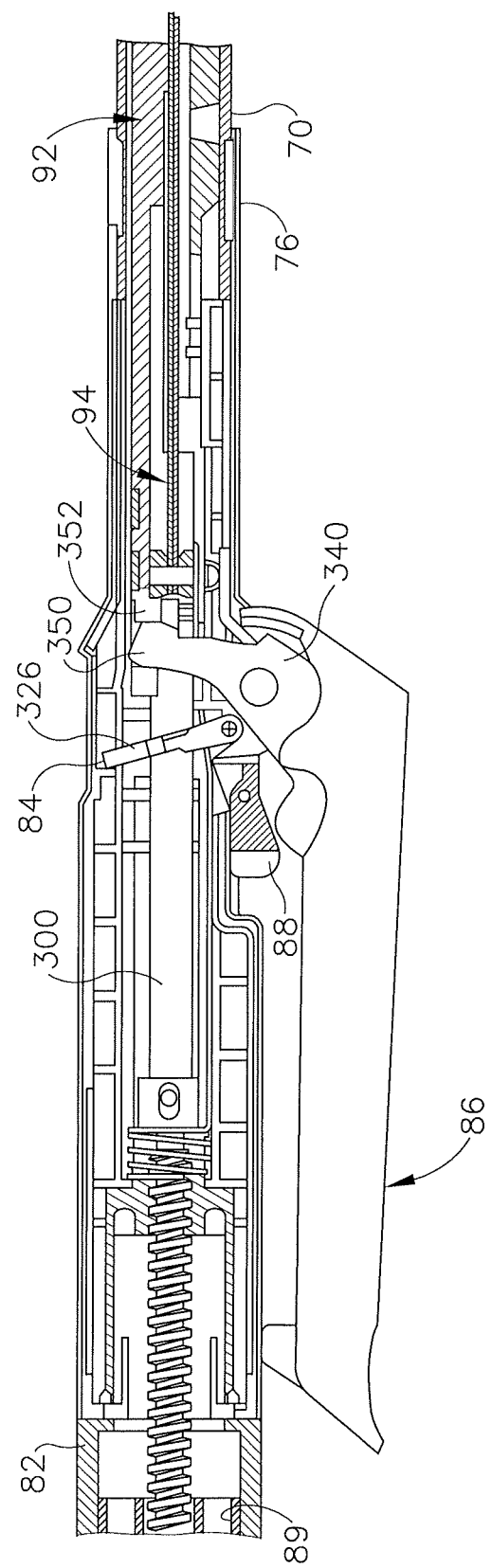
FIG. 7 depicts a side, cross sectional view of the actuator handle assembly of FIG. 5 in a fired position.

When the gap between anvil (102) and staple holder (68) is set to produce a desired staple height within the operating range of stapling instrument (50), safety latch (88, 488, 588, 688) is pivoted upward (FIGS. 6, 9, 11, 13, 19, 22 and 24) to disengage staple actuating lever (86). In the pivoted position, safety latch (88, 488, 588, 688) engages either control rod (300, 400) or adjusting knob (82, 682, 782, 882) to prevent rotation of adjusting knob (82, 682, 782, 882) and to thereby maintain the selected staple height. Stapling instrument (50) is fired by grasping and pivoting staple actuating lever (86) clockwise, as viewed in FIG. 7, to move staple actuating lever (86) to its fired position. As a result, actuator fingers (350) on trigger arm (340) drive firing clip (352) in the distal direction to advance driver actuating member (92) longitudinally along shaft assembly (70). Driver actuating member (92) advances staple driver (62) to move driver fingers (63) distally in staple receiving slots (65) to engage staples (90). Driver actuating member (92) transmits the required motion and compressive forces from trigger arm (340) to staple driver (62) to drive staples (90) from staple holder (68) into the tissue and against anvil (102). Also, circular knife (69) is advanced by staple driver (62) to cut the tissue against backup washer (160). As shown in FIG. 4, circular knife (69) splits backup washer (160) into two annular sections. Staples (90) join the ends of tissue sections (52) and (54) with a fluid tight seal formed by concentric annular rows of staples (90). Circular knife (69) cuts away excess tissue within the anastomosis near the stapled region. The severed excess tissue may be trapped within stapling head assembly (60) (e.g., between the interior of circular knife and the exterior of the assembly of trocar (73) and anvil shaft (104)).

After the stapling and cutting of the tissue is completed, staple actuating lever (86) is biased by spring (346) to its fully open position (FIG. 6). Actuator fingers (350) of trigger arm (340) pivot counterclockwise, as viewed in FIG. 6, to move firing clip (352) and driver actuating member (92) in the proximal direction. As a result, staple driver (62), which is connected by locator fingers (230) to driver actuating member (92), and circular knife (69) are retracted into stapling head assembly (60). In case of entrapment of staples, tissue or other debris between staple holder (68) and driver fingers (63), the retraction of staple driver (62) frees stapling head assembly (60) from the tissue before stapling instrument (50) is withdrawn from the patient. If a high force is required, staple actuating lever (86) can be returned manually to its fully advanced position to retract staple driver (62).

Next, safety latch (88, 488, 588, 688) is pivoted downward to lock staple actuating lever (86) and release adjusting knob (82, 682, 782, 882) so that adjusting knob (82, 682, 782, 882) may freely rotate. The stapled tissue between anvil (102) and staple holder (68) is released by rotating adjusting knob (82) counterclockwise to advance anvil assembly (100) away from stapling head assembly (60). Anvil (102) is moved through the lumen by manipulating the stapled tissue in a suitable manner to slip the anvil through the stapled lumen. Then, stapling instrument (50) is withdrawn from the patient leaving behind the stapled lumen between tubular tissue sections (52) and (54).

II. Exemplary Actuator Safety Switch with Brake

It will be appreciated that inadvertent firings are generally undesirable and may be caused for a variety of reasons. In some instances, inadvertent firings may be caused simply through unintentional contact with actuating lever (86) after safety latch (88) has been flipped up (FIG. 6). Thus, it may be desirable to prevent movement of actuating lever (86), even after movable indicator (84) is positioned in scale (87) and safety latch (88) is flipped up, until the user is ready to insert staples into tissue. In some instances, inadvertent or incomplete firings may be caused by firing stapling instrument (50) when anvil assembly (100) is not properly placed on anvil shaft (104). Thus, in those instances, it may be desirable to prevent the firing of surgical instrument (50) until anvil assembly (100) is properly placed on anvil shaft (104). It will further be appreciated that firings may be generally undesirable if movable indicator (84) is not positioned in scale (87) (i.e., when the anvil gap is outside of the "green zone").

Figure 9:
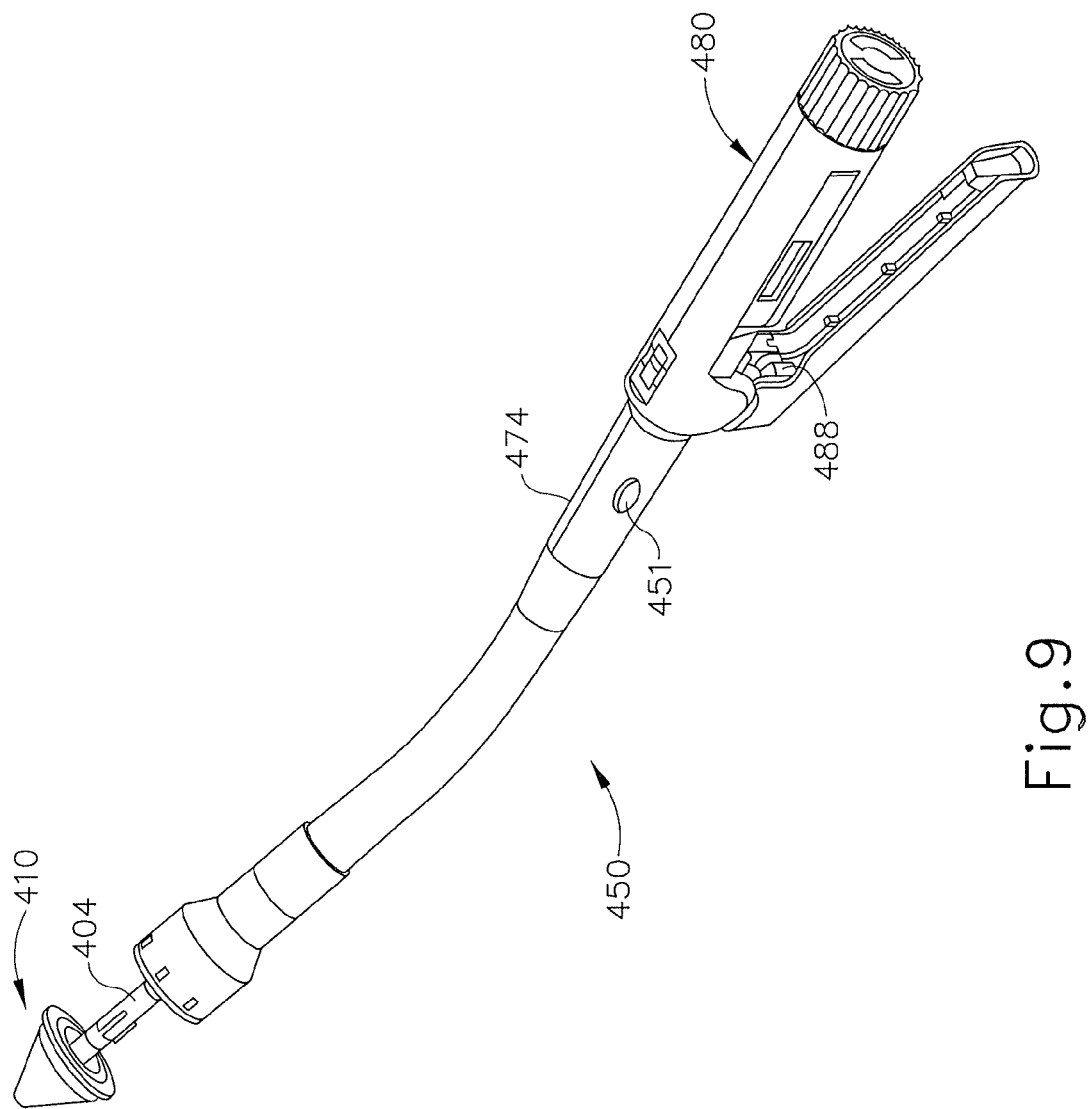
FIG. 9 depicts a perspective view of an exemplary stapler instrument with a safety feature.

FIG. 9 shows an exemplary stapling instrument (450) comprising an anvil assembly (410) mounted on a shaft (404). Stapling instrument (450) of FIG. 9 operates substantially similar to stapling instrument (50) described above. Stapling instrument (450) comprises an actuator safety switch (451). Actuator safety switch (451) in the present example is positioned on tubular extension (474). Furthermore, actuator safety switch (451) is positioned on tubular extension (474) such that a user is unlikely to inadvertently trigger actuator safety switch (451) as the user holds actuator handle assembly (480) to position stapling instrument (450) for stapling. FIG. 10 shows a side view of actuator safety switch (451) as actuator safety switch (451) is in communication with driver actuating member (492) within tubular extension (474). Actuator safety switch (451) comprises two opposingly oriented buttons and/or actuators that may be pressed by squeezing the buttons and/or switches toward each other. Actuator safety switch (451) is in communication with brake pads (453), which squeeze driver actuating member (492). Such squeezing by brake pads (453) provides friction that substantially prevents driver actuating member (492) from translating longitudinally, such that brake pads (453) substantially prevent motion and compressive forces to staple driver (62).

In the present example, actuator safety switch (451) is connected to brake pads (453) through a scissoring mechanism such that the user may actuate brake pads (453) by squeezing actuator safety switch (451). In some versions, brake pads (453) are resiliently biased to grip driver actuating member (492). Thus, when a user squeezes actuator safety switch (451), brake pads (453) release driver actuating member (492). While brake pads (453) selectively grip driver actuating member (492) in the present example, it will be appreciated that brake pads (453) may grip any suitable component of stapling instrument (450) in order to prevent firing of stapling instrument (450) until the user manually releases brake pads (453). In some versions, brake pads (453) prevent the movement of driver actuating member (492) through a frictional grip. As another merely illustrative variation, brake pads (453) may prevent movement of driver actuating member (492) by mechanically coupling with driver actuating member (492). For example, brake pads (453) may have pawls operable to engage teeth on driver actuating member (492) such that when engaged, brake pads (453) prevent movement of driver actuating member (492). As yet another merely illustrative variation, brake pads (453) may be equipped with teeth where driver actuating member (492) is equipped with pawls. Other suitable variations will be apparent to one of ordinary skill in the art in view of the teachings herein.

In some versions, actuator safety switch (451) acts in isolation from other components of stapling instrument (450) such that the user can simply operate actuator safety switch (451) to enable driver actuating member (492) to translate staple driver (62). In some versions, actuator safety switch (451) is in communication with safety latch (488) through, for example, a communication rod or linkage, electrical communication, etc. or any other suitable communication mechanism such that actuator safety switch (451) is not operable to release brake pads (453) until safety latch (488) is released. Thus, during operation in some versions, safety latch (488) must first be actuated before actuator safety switch (451) may be squeezed to release brake pads (453). For example, FIG. 11 shows safety latch (488) engaged such that actuating lever (486) cannot be actuated. In addition, actuator safety switch (451) cannot release brake pads (453) to release driver actuating member (492) until safety latch (488) is released.

Figure 19A:
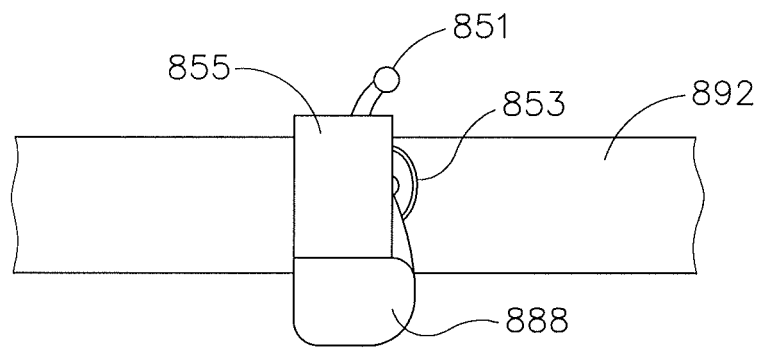
FIG. 19A depicts a side view of a brake and driver actuating member inside the stapler instrument, with a mechanical linkage in a first position to restrict movement of the brake and driver actuating member.
Figure 19B:
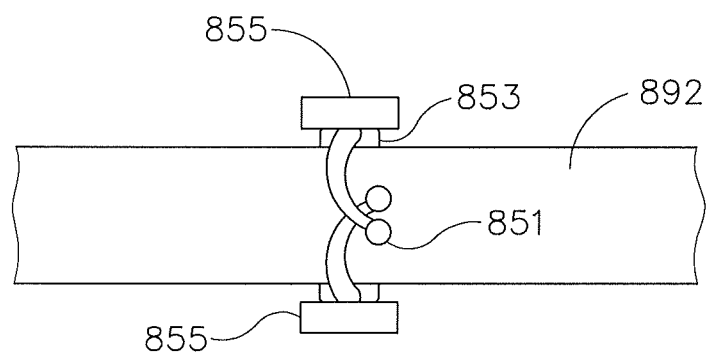
FIG. 19B depicts a top view of a brake, driver actuating member, and mechanical linkage of FIG. 19A inside the stapler instrument, with the mechanical linkage in the first position.
Figure 19C:
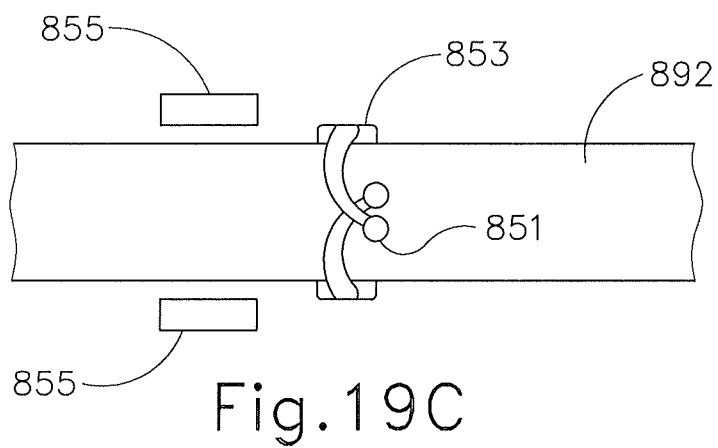
FIG. 19C depicts a top view of a brake, driver actuating member, and mechanical linkage of FIG. 19A inside the stapler instrument, with the mechanical linkage moved to a second position to enable outward movement of the brake and driver actuating member.

FIGS. 19A-19C show a merely illustrative variation where a mechanical linkage (855) is coupled with safety latch (888), such that mechanical linkage (855) moves longitudinally in response to pivoting of safety latch (888). When safety latch (888) is positioned to prevent actuation of a staple actuating lever (such as staple actuating lever (86) described above, etc.), mechanical linkage (855) is positioned to block outward movement of brake pads (853) as shown in FIGS. 19A-19B. Mechanical linkage (855) thus keeps brake pads (853) in engagement with driver actuating member (892), thereby preventing driver actuating member (892) from driving staples into tissue, when in the position shown in FIGS. 19A-19B. When safety latch (888) is moved to a position to permit actuation of the staple actuating lever, mechanical linkage (855) is positioned to enable outward movement of brake pads (853) as shown in FIG. 19C, to thereby release and enable driver actuating member (892) to drive staples into tissue. The user may freely manipulate actuator safety switch (851) to release brake pads (853), thereby allowing driver actuating member (892) to communicate motion, once safety latch (888) and mechanical linkage (855) are moved to the position shown in FIG. 19C. Thus, brake pads (853) are prevented from releasing driver actuating member (892) until safety latch (888) is flipped to provide clearance for movement of the staple actuating lever.

As another merely illustrative variation (not shown), actuator safety switch (451) may be coupled to safety latch (488) such that actuator safety switch (451) engages brake pads (453) to grip driver actuating member (492) only after safety latch (488) is disengaged. In other words, initially, safety latch (488) operates to prevent firing of stapling instrument (450) until safety latch (488) is disengaged. Brake pads (453) are disengaged from driver actuating member (492) while safety latch (488) engages actuating lever (486). Once safety latch (488) is disengaged from actuating lever (486), brake pads (453) engage driver actuating member (492) to prevent stapling instrument (450) from firing. In some versions, brake pads (453) may disengage driver actuating member (492) by the user operating a manual release, by re-engaging safety latch (488) and/or safety switch (451). Furthermore, in some versions, safety switch (451) may be inoperable until movable indicator (84) moves into the zone shown by scale (87). In addition or in the alternative, safety switch (451) may be inoperable until anvil assembly (410) is fully seated on shaft (404) or a trocar, such as one shown in FIG. 2. Once safety switch (451) has been enabled and is preventing movement of driver actuating member (492), the user may press actuator safety switch (451) to release brake pads (453) from driver actuating member (492), thereby allowing stapling instrument (450) to fire.

In yet other exemplary versions, actuator safety switch (451) may comprise two separately operable buttons and/or switches where one button/switch is operable to cause brake pads (453) to grip and prevent movement of driver actuating member (492), and where the other button/switch is operable to cause brake pads (453) to release driver actuating member (492). In some versions, actuator safety switch (451) may comprise a single switch operable to be switched between two or more positions, where each position of actuator safety switch (451) corresponds to a different action for brake pads (453). For example, one position of actuator safety switch (451) causes brake pads (453) to grip driver actuating member (492), whereas another position of actuator safety switch (451) causes brake pads (453) to release driver actuating member (492). Other suitable components, features, configurations, and operabilities that may be included in safety switch (451) will be apparent to one of ordinary skill in the art in view of the teachings herein.

III. Exemplary Actuator Safety Switch with Pin

Figure 12:
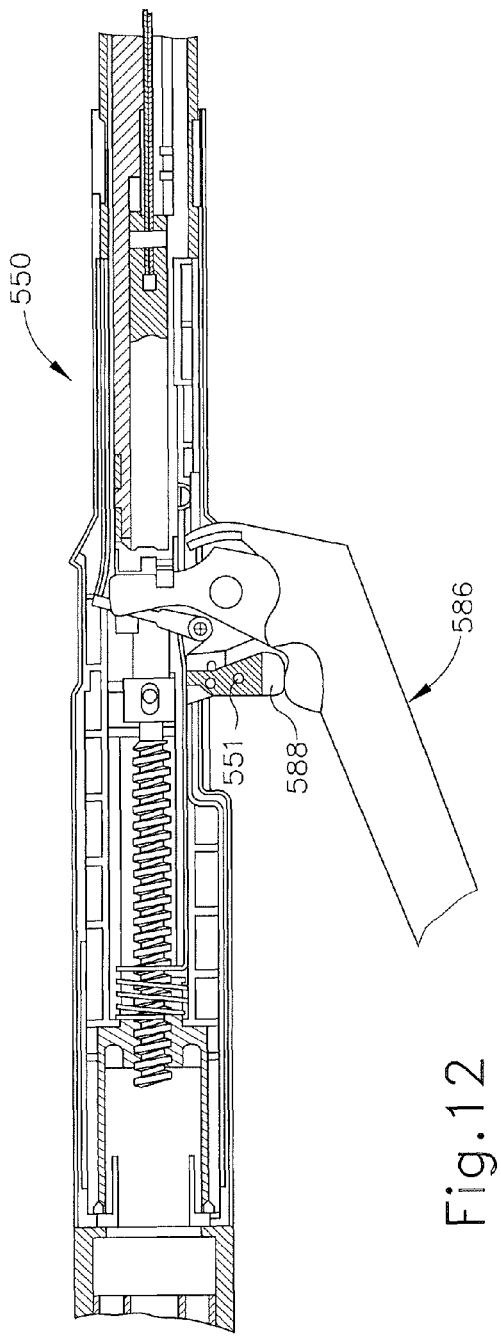
FIG. 12 depicts a side cross sectional view of another exemplary stapler instrument having a safety feature.
Figure 14:
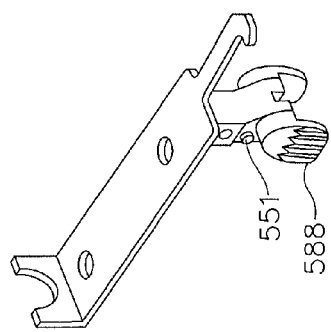
FIG. 14 depicts a perspective view of the safety feature of FIG. 12 in an unlocked position.
Figure 13:
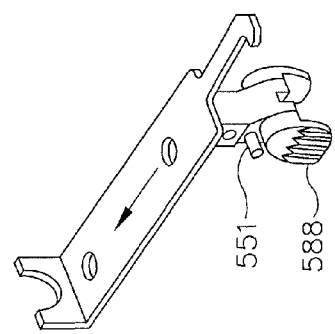
FIG. 13 depicts a perspective view of the safety feature of FIG. 12 in a locked position.

It will be appreciated that in some instances, inadvertent firings may be prevented by providing an additional manually operable way of controlling a safety switch (588) such that safety switch (588) is not inadvertently flipped. FIGS. 12-14 show an exemplary version of stapling instrument (550) where safety switch (588) comprises a safety feature in the form of a peg (551) that is operable to prevent inadvertent releasing of safety switch (588). Peg (551) is movable between a blocked position and an unblocked position. In the blocked position as shown in FIG. 13, peg (551) prevents safety switch (588) from being moved, such that safety switch continues to prevent the user from being able to move staple actuating lever (586). In the unblocked position, as shown in FIG. 14, peg (551) enables the safety switch (588) to be moved, to thereby enable movement of staple actuating lever (586). Thus, in operation, when anvil assembly (100) is appropriately positioned and the user is prepared to fire stapling instrument (550), the user first moves peg (551) from the blocked position to the unblocked position, thereby allowing safety switch (588) to be released and stapling instrument (550) to be fired. Peg (551) of this example has a cylindrical shape, though it should be understood that any other suitable shape or configuration may be used. For example, pin (551) may be substituted or supplemented with a latch, a sliding lock, etc. or any other suitable mechanism operable to selectively prevent safety switch (588) from moving.

Figure 15:
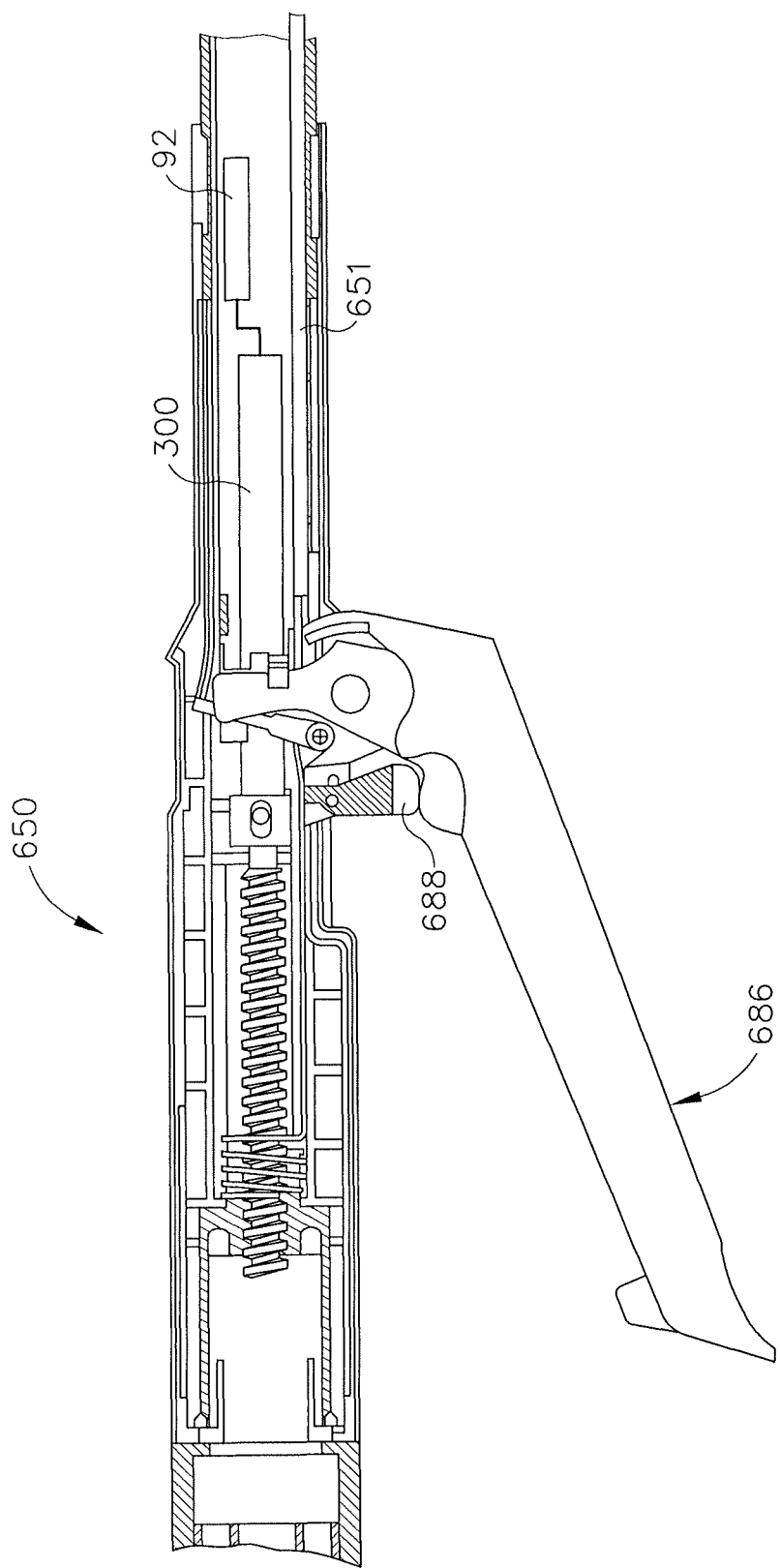
FIG. 15 depicts a side, cross sectional view of an exemplary stapler instrument having an alternative safety feature.

In some instances, an incomplete firing may be caused by anvil assembly (100) not being positioned properly on anvil shaft (104). FIG. 15 shows an exemplary version of a stapling instrument (650) having a feature that is operable to verify that anvil assembly (100) is positioned properly on anvil shaft (104) before allowing stapling instrument (650) to fire. Stapling instrument (650) is understood to be substantially similar to stapling instrument (550) shown in FIG. 12, though stapling instrument (650) of this example further comprises an anvil rod (651). Anvil rod (651) extends longitudinally through stapling instrument (650) and is in communication with anvil assembly (100). As anvil assembly (100) is placed on anvil shaft (104), anvil rod (651) is pushed proximally. When anvil assembly (100) is not connected to anvil shaft (104), anvil rod (651) is distally biased by, for example, a spring, piston, resilient wire, or any other suitable distally biasing mechanism. It should be noted that FIG. 15 shows driver actuating member (92) and control rod (300) in schematic form, just for clarity. Driver actuating member (92) and control rod (300) of this example may be configured and operable just like the same components described above. Anvil rod (651) may be positioned alongside driver actuating member (92) and control rod (300) and may freely translate within shaft (70).

FIGS. 17A-17B show a pivoting safety switch (688) with anvil rod (651) extending through safety switch (688). Safety switch (688) includes a safety opening (655) that is shaped and sized to fit a pin (657) inserted into safety opening (655). As shown in FIG. 16, pin (657) of this example has a dumbbell shape with a first lobe (670) and second lobe (672) connected by a middle portion (674). It should be understood, however, that pin (657) may have any other suitable shape may be used as would be apparent to one of ordinary skill in the art in view of the teachings herein. For example, an elongate rod having a smaller middle and larger ends may be used for pin (657). It will be appreciated that pin (657) is sized to fit completely through safety opening (655), such that pin (657) may pass entirely through safety opening (655) in either direction. When pin (657) is positioned within safety opening (655), pin (657) prevents safety switch (688) from being actuated, such that actuating lever (686) is locked in place by safety switch (688). When pin (657) is removed from safety opening (655), safety switch (688) may be actuated to allow actuating lever (686) to move, thereby allowing stapling instrument (650) to fire.

As seen in FIG. 18, anvil rod (651) defines an opening (653) positioned on a proximal end of anvil rod (651). Pin (657) is sized and shaped with fit through safety opening (655). Opening (653) of anvil rod (651) has a smaller portion (660) and a larger portion (662). Pin (657) and opening (653) are sized such that pin (657) can pass through larger portion (662), but not smaller portion (660). When anvil rod (651) is distally advanced (i.e. anvil not fully seated on shaft) as shown in FIG. 17A, smaller portion (660) of opening (653) is aligned with pin (657), which prevents pin (657) from being removed from opening (653). When anvil rod (651) is proximally positioned (i.e. anvil fully seated on shaft) as shown in FIG. 17B, larger portion (662) of opening (653) is aligned with pin (657), thus allowing pin (657) to be removed from opening (653). As a result, anvil assembly (100) may effectively be used to control anvil rod (651) to align either smaller portion (660) or larger portion (662) of opening (653) with pin (657).

Initially, pin (657) is aligned with smaller portion (660). As a result, safety switch (688) remains engaged so as to prevent the user from operating stapling instrument (650). Once anvil assembly (100) is properly placed on anvil shaft (104), anvil rod (651) moves proximally in relation to pin (657) such that pin (657) aligns with larger portion (662) of opening (653), thereby allowing pin (657) to be removed such that safety switch (688) may be actuated. It will be appreciated that such proximal movement of anvil rod (651) can only occur if anvil assembly (100) is placed completely on anvil shaft (104). Thus, safety switch (688) can only be actuated when anvil assembly (100) is properly placed on anvil shaft (104). In FIG. 18, opening (653) is shown as having a generally dumbbell-type shape; however, any suitable shape for opening may be used as would be apparent to one of ordinary skill in the art in view of the teachings herein.

In any of the above versions of stapling instrument (50, 450, 550, 650), it will be appreciated that once stapling instrument (50, 450, 550, 650) has fired, anvil assembly (100) may be distally moved such that stapling instrument (50, 450, 550, 650) can be removed from the surgical site. It will be appreciated that as stapling instrument (50, 450, 550, 650) is removed from the surgical site, it may be desirable to avoid firing stapling instrument (50, 450, 550, 650) again. In the exemplary version, stapling instrument (50, 450, 550, 650) uses adjusting knob (82), as shown, for example, in FIG. 1, which may be used to close or widen gap between anvil assembly (100) and stapling head assembly (60). In some versions, anvil rod (751) may be coupled to adjusting knob (82) such that if adjusting knob (82) is rotated a predetermined amount after stapling instrument (50, 450, 550, 650) completes a firing cycle, anvil rod (751) may be move distally such that safety switch (688) re-engages actuating lever (686) to lock-out actuating lever (686) from firing. In some versions, it will be appreciated that adjusting knob (82) may be mechanically coupled to any suitable safety related component such that when the user turns adjustment knob (82) in a particular direction after the surgical procedure, stapling instrument (50, 450, 550, 650) is prevented from firing again.

It may also be desirable to prevent stapling instrument (50, 450, 550, 650) from firing a second time (e.g., inadvertently) after stapling instrument (50, 450, 550, 650) has been fired successfully once. Thus, in some versions, safety switch (88, 488, 588, 688) may be spring-biased such that safety switch (88, 488, 588, 688) springs back into place after a successful firing of stapling instrument, thereby preventing the user from inadvertently operating actuating lever (86, 486, 586, 686) more than once. In some such versions, the user may subsequently disengage safety switch (88, 488, 588, 688) such that actuating lever (86, 486, 586, 686) can be operated again, but such functionality is not required and in some cases may not be desirable.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I/We claim:

1. A surgical stapler comprising:
   (a) an end effector, wherein the end effector is operable to drive a plurality of staples into tissue;
   (b) a driver operable to actuate the end effector to drive the plurality of staples into tissue;
   (c) a trigger in communication with the driver, wherein the trigger is operable to actuate the driver to thereby actuate the end effector;
   (d) a safety switch in communication with the trigger, wherein the safety switch is moveable between a locked position and an unlocked position, wherein the safety switch is operable to prevent operation of the trigger when the safety switch is in the locked position, wherein the safety switch is operable to enable operation of the trigger when the safety switch is in the unlocked position; and
   (e) a safety feature in communication with the safety switch, wherein the safety feature is configured to prevent operation of the driver when the safety switch is in the unlocked position;
      wherein the safety feature is configured to engage the driver after a portion of tissue has been stapled.

2. The surgical stapler of claim 1, wherein the safety switch comprises a pivoting member operable to block movement of the trigger.

3. The surgical stapler of claim 1, wherein the safety feature comprises an actuating switch and a braking assembly.

4. The surgical stapler of claim 3, wherein the driver is in communication with a translating driver actuating member, wherein the braking assembly is in communication with the driver actuating member.

5. The surgical stapler of claim 4, wherein the actuating switch is operable to control the braking assembly such that the braking assembly is operable to selectively grip or release the driver actuating member.

6. The surgical stapler of claim 5, wherein the actuating switch comprises at least one button, wherein the at least one button is operable to be actuated between at least two positions, wherein the at least one button is configured to direct brake pads to grip the driver actuating member, wherein the at least one button is further configured to direct the brake pads to release the driver actuating member.

7. The surgical stapler of claim 1, further comprising an anvil rod extending between the safety switch.

8. The surgical stapler of claim 7, wherein the anvil rod is operable to selectively block movement of the safety switch.

9. The surgical stapler of claim 8, wherein the end effector comprises an anvil assembly and an anvil shaft, wherein the anvil rod is configured to move proximally or distally based on whether the anvil is attached to the anvil shaft.

10. The surgical stapler of claim 9, wherein the anvil rod is configured to communicate the connection status between the anvil and the anvil shaft to a visible indicator.

11. The surgical stapler of claim 1, wherein the safety switch and the safety feature are operable to be simultaneously actuated by a single hand.

12. The surgical stapler of claim 1, wherein the safety feature is configured to be re-engaged after a single use of the surgical stapler.

13. A surgical stapler comprising:
   (a) an end effector, wherein the end effector is operable to drive a plurality of staples into tissue;
   (b) a driver operable to actuate the end effector to drive the plurality of staples into tissue;
   (c) a trigger in communication with the driver, wherein the trigger is operable to actuate the driver to thereby actuate the end effector;
   (d) a safety switch in communication with the trigger, wherein the safety switch is moveable between a locked position and an unlocked position, wherein the safety switch is operable to prevent operation of the trigger when the safety switch is in the locked position, wherein the safety switch is operable to enable operation of the trigger when the safety switch is in the unlocked position; and
   (e) a safety feature in communication with the safety switch, wherein the safety feature is configured to prevent operation of the driver when the safety switch is in the unlocked position;
      wherein the safety feature comprises an actuating switch and a braking assembly;
      wherein the driver is in communication with a translating driver actuating member, wherein the braking assembly is in communication with the driver actuating member;
      wherein the actuating switch is operable to control the braking assembly such that the braking assembly is operable to selectively grip or release the driver actuating member.

* * * * *